United States Patent [19]

Leung et al.

[11] Patent Number: 5,286,623
[45] Date of Patent: Feb. 15, 1994

[54] METHOD FOR SCREENING FOR KAWASAKI DISEASE

[75] Inventors: Donald Y. M. Leung, Englewood; Brian Kotzin; Jun Abe, both of Denver, all of Colo.

[73] Assignee: National Jewish Center for Immunology and Respiratory Medicine, Denver, Colo.

[21] Appl. No.: 2,520

[22] Filed: Jan. 11, 1993

Related U.S. Application Data

[63] Continuation of Ser. No. 801,772, Nov. 26, 1991, abandoned.

[51] Int. Cl.$^5$ .................. C12Q 1/68; C12P 19/34; G01N 33/53
[52] U.S. Cl. ......................... 435/6; 435/7.24; 435/91
[58] Field of Search .................. 435/7.24, 6, 91

[56] References Cited

U.S. PATENT DOCUMENTS 4,886,743 12/1989 Hood et al. ..................... 435/5

OTHER PUBLICATIONS

Abe et al., "Selective expansion of T cells expressing T-Cell receptor variable regions VB2 and VB8 in Kawasaki disease", Proc. Natl. Acad. Sci. USA 89 4066–4070 (May 1992)–not prior art.
Yanagihara et al., "Acute Fibrille Mucocutaneous Lymph Node Syndrome", Am. J. Dis. Child 134: 603–613 (Jun., 1980).
Toyonga et al., "Genes of the T-Cell Antigen Receptor In Norman and Malignant Cells", Ann. Rev. Immunol. 5: 565–620 (1987).
White et al., "The VB-Sepcific Superantigen Staphlococal Entertoxin B:Stimulation of Mature T Cell and Clonal Deletion in Neonatal Mice", Cell 56: 27–35 (Jan. 13, 1989).
Kappler et al., "VB-Specific Stimulation of Human T Cells by Staphylococcal Toxins", Science 244: 811–813 (May 19, 1989).
Choi et al., "Interaction of Staphylococcus aureus toxin 'superantigens' with human T cells", Proc. Natl. Acad. Sci. USA 86: 8941–8945 (Nov. 1989).
Leung et al., "Immunologic Aspects of Kawaski Disease Syndrome", J. Rheumatol (suppl 24: 15–17 (1990)).
Choi et al., "Selective Expansion of T Cells Expressing VB2 in Toxic Shock Shock Syndrome", J. Exp. Med. 172: 981–984 (Sep. 1990).
Choi et al., "A method for production of antibodies to human T-cell receptor B-chain variable regions", Proc. Natl. Acad. Sci. USA 88: 8537–8361 (Oct. 1991).
Kim et al. Reduction of lupus nephritis in MRL/lprmice by a bacterial superantigen treatment. J. Exp. Med (Dec. 1991) 174:1431–1437.
Leung, et al. Reversal of lymphocyteactivation in vivo in the Kawasaki syndrome by intravenous gamma globulin, J. Clin. Invest (Feb. 1987) 79:468–472.
Pullen, et al. Identification of the region of T cell receptor B chain that interacts with the self-superantigen MIS-19. Cell (Jun. 29, 1990) 61:1365–1374.

*Primary Examiner*—Margaret Parr
*Assistant Examiner*—David Schreiber
*Attorney, Agent, or Firm*—Felfe & Lynch

[57] ABSTRACT

The invention relates to screening of patients to determine the possible presence of Kawasaki Disease. The screening involves assaying for levels of V$\beta$2 or V$\beta$8.1 by immunoassay, or for the mRNA expressing either of these V$\beta$ elements. The polymerase chain reaction is one way the mRNA level can be determined. Once the levels in the patient are determined, they are compared to normal levels. An increase is indicative of possible Kawasaki Disease.

7 Claims, 5 Drawing Sheets

METHOD FOR SCREENING FOR KAWASAKI DISEASE

The invention described herein was funded in part by USPHS Grant HL-37260. The U.S. government may have certain rights herein.

This application is a continuation of application Ser. No. 07/801,772, filed Nov. 26, 1991, now abandoned.

FIELD OF THE INVENTION

This invention relates to the diagnosis of diseases or conditions wherein changes in the level of certain elements of the T cell receptor (TCR) repertoire vary from normal levels. More particularly, it relates to the diagnosis of vasculitic disorders and conditions via assaying for particular $V\beta$ elements in a sample taken from a patient. In addition it relates to therapies based on the observations arising out of the diagnostic methods.

RELATED APPLICATIONS

The assignee of this application has also filed U.S. patent applications Ser. Nos. 435,370, 488,353 and 732,114, all of which deal with the assaying of the T cell repertoire of a patient.

BACKGROUND AND PRIOR ART

In recent years, the mechanism by which mammalian immune systems, such as human and murine systems react to infections, foreign antigens, and to so-called "self antigens" in connection with autoimmune diseases has begun to be established. See, in this regard, Grey et al., Scientific American 261(5): 56-64 (1989); Male et al., *Advanced Immunology* (J. P. Lippincott Company, 1987), especially chapters 6 through 10.

Well known, both to the skilled artisan and to the general public is the role of antibodies, sometimes referred to as "immunoglobulin" or the less correct and older "gammaglobulin" in response to infection. Antibodies are protein molecules which are produced by B cells in response to infection. It is well known that these antibodies act to "disable" or to inactivate infectious agents in the course of combating the infection.

In order for antibodies to be produced, however, preceding events must occur which lead to stimulation of the B cells which produce the antibodies. One of the key events involved in the processes leading to antibody production is that of antigen recognition. This aspect of the immune response requires the participation of so-called "T-cells", and is less well known than the antibody response commented on supra.

Briefly, and in outline form, antigen recognition requires interaction of an "antigen presentation cell", a "processed antigen", and a T-cell. See Grey and Male, supra. The "processed antigen", in an infection, is a molecule characteristic of the pathogen which has been treated, i.e., "processed", by other cells which are a part of the immune system. The processed antigen interacts with a receptor on the surface of an antigen presentation cell in a manner not unlike a lock fitting into a key hole or, perhaps more aptly, two pieces of a jigsaw puzzle.

The configuration of the complex of processed antigen and receptor on antigen presentation cell allows the participation of T-cells. T-cells do not join the complex unless and until the processed antigen has fit into the receptor on the antigen presentation cell. This receptor will hereafter be referred to by its scientific name, the major histocompatibility complex (MHC), or the human leukocyte antigen (HLA). Generally, MHC is used to refer to murine systems, and HLA to humans.

These receptors fall into two classes. MHC-II molecules are involved in most responses to pathogens. In contrast, MHC-I molecules are involved when the pathogen is a virus, or when a malignant cell is involved. When MHC-I participation is involved, there is no antibody stimulation; rather, the interaction of MHC-I, processed antigen and T-cell leads to lysis of cells infected with the pathogen.

The foregoing discussion has focused on the events involved in responding to "infection", i.e., the presence of pathogenic foreign material in the organism. Similar mechanisms are involved in autoimmune diseases as well. In these conditions, the organism treats its own molecules as foreign, or as "self-antigens". The same type of complexing occurs as described supra, with an antibody response being mounted against the organism itself. Among the diseases in which this is a factor are rheumatoid arthritis, diabetes, systemic lupus erythromatosus, and others.

The ability of the T-cell to complex with the processed antigen and MHC/HLA complex is dependent on what is referred to as the T-cell antigen receptor, referred to as "TCR" hereafter. The TCR is recognized as a heterodimer, made up of alpha ($\alpha$) and beta ($\beta$) chains. Five variable elements, coded for by germline DNA and known as "$V\alpha$, $J\alpha$, $V\beta$, $D\beta$, and $J\beta$" as well as non-germline encoded amino acids contribute to the TCR. See, in this regard, Marrack, et al., Immunol. Today 9: 308-315 (1988); Toyonaga et al., Ann. Rev. Immunol. 5: 585-620 (1987); Davis, Ann. Rev. Immunol. 4: 529-591 (1985); Hendrick et al., Cell 30:1 41-152 (1982). With respect to the binding of TCR with processed antigen and MHC, see Babbitt et al., Nature 317: 359-361 (1985); Buus et al., Science 235: 1353-1358 (1987); Townsend et al., Cell 44: 959-968 (1986); Bjorkman et al., Nature 329: 506-512 (1987).

Generally, both the alpha and beta subunits are involved in recognition of the ligand formed by processed antigen and MHC/HLA molecule. This is not always the case, however, and it has been found that so-called "superantigens" stimulate T-cells with a particular $V\beta$ element, regardless of any other element. See Kappler et al., Cell 49: 273-280 (1987); Kappler et al., Cell 49: 263-271 (1987); MacDonald et al., Nature 332: 40-45 (1988); Pullen et al., Nature 335: 796-801 (1988); Kappler et al., Nature 332: 35-40 (1988); Abe et al., J. Immunol 140: 4132-4138 (1988); White et al., Cell 56: 27-35 (1989); Janeway et al., Immunol. Rev. 107: 61-88 (1989); Berkoff et al., J. Immunol. 139: 3189-3194 (1988), and Kappler et al., Science 244: 811-813 (1989).

The "superantigens" mentioned supra, while generally stimulating T-cells, are somewhat specific in terms of the particular form of the $V\beta$ moiety which is present on the stimulated T cell. This feature is one aspect of the invention, i.e., the ability to assay for particular subtypes or subclasses of T-cells, based upon the cell surface antigens presented by these subclasses.

It must be pointed out, however, that the expansion of the $V\beta$ element does not in and of itself mean that a superantigen is involved, and in the discussion which follows, the inventors do not limit themselves to the possibility that vasculitic disorders are caused by a superantigen mechanism.

Staphylococcus antigens discussed supra are not the only substances which provoke a restricted, $V\beta$ proliferative response. Indeed, it is the purpose of this invention to show that such a response occurs, and can be measured in other diseases and conditions, vasculitic disorders in particular, even where an etiological agent is not recognized. It is the purpose of this invention to provide a method for diagnosing a vasculitic disorder by assaying a T-cell containing sample from a patient for a particular $V\beta$ element, and comparing the value determined to "base line" or "normal" values. Deviation from normal is indicative of the particular vasculitic disease associated with variations in the level of the particular $V\beta$ element. In a particularly preferred embodiment, the method is used for diagnosis of Kawasaki disease, but other vasculitic disorders, such as Wegener's Granulomatosis, Systemic Lupus Erythematosis, Behcet's disease, Chung-Strauss Syndrome, Lymphomatoid Granulomatosis, juvenile rheumatoid arthritis, Polyarteritis Nodosa, Rheumatic Fever, and Thromboangiitis Obliterans may also be diagnosed in the manner described herein.

In a particularly preferred embodiment, the $V\beta$ element is assayed for by utilizing polymerase chain reaction ("PCR"), as described in, e.g., U.S. Pat. Nos. 4,683,195; 4,800,159 and 4,683,202 the disclosures of which are incorporated by reference. Another preferred method involves assaying the $V\beta$ element by use of antibodies, monoclonal antibodies in particular.

The data which follow deal, for the most part with Kawasaki Disease, and to that end some discussion is necessary.

Sometimes referred to as monocutaneous lymph note syndrome, Kawasaki disease ("KD" hereafter) is an acute multi system vasculitis of unknown etiology. The disease primarily affects infants and young children. See Kawasaki, Jpn. J. Allergol 16: 178–222 (1967); Rauch et al., Pediatr. Infect. Dis. 4: 702–703 (1985). While KD does occur worldwide, it is most prevalent in Japan and in children of Japanese ancestry. Primary clinical manifestations include prolonged fever, bilateral non-exudative conjuctivitis, induration and erythema of extremities, inflammation of lips and oropharynx, polymorphous skin rash, and cervical lymphadenopathy.

In Japan and in the United States, KD has become one of the most common causes of acquired heart disease in children. Recent studies have shown that when gamma globulin is administered intravenously ("IVGG") during the acute phase of the disease, coronary artery lesions, which otherwise develop in 15-25% of patients, are significantly decreased. See Newburger et al., N. Engl. J. Med. 315: 341–6 (1986); Nagashima et al., J. Pediatr. 110: 710–2 (1987); Firisho et al., Lancet ii: 1055–57 (1984); Rowley et al., J. Pediatr. 113: 290–94 (1988); Newburger et al., N. Eng. J. Med. 324: 1633 39 (1991). Thus, in order to treat this disease effectively, as with all other vasculitic diseases, early recognition is essential.

KD is characterized by an acute stage, as well as a convalescent stage. These are described in some detail infra. The acute phase is characterized, inter alia, by marked immune activation. Investigators have demonstrated, for example, increased numbers of circulating and infiltrating T cells bearing the HLA-DR activation antigen and elevated serum soluble IL-2 receptor levels. The phenomena are indicative of T-cell activation. See Leung et al., J. Clin. Invest. 79: 468–472 (1987); Terai et al., Hum. Pathol. 21: 231–234 (1990); Lang et al., J. Pediatr. 116: 592–596 (1990). In addition, acute KD has been associated with increased production of IL-1$\beta$, TNF-$\alpha$, IL-6, IL-2, and IFN-$\gamma$. See, e.g., Matsubara et al., Clin. Immunol. Immunopathol 56: 29–36 (1990); Maury et al., J. Lab. Clin. Med. 113: 651–54 (1989); Lang et al., J. pediatr. 115: 939–43 (1989); Leung et al., Lancet ii: 1928–1302 (1989); Rowley et al., Ped. Inf. Dis. J. 7: 663–67 (1988); Ueno et al., Clin. Exp. Immunol 76: 337–342 (I989); Jordan et al., in Kawasaki, ed., The Third International Kawasaki Disease Symposium 1989: 144–46. The cytokines referred to supra are believed to play a significant role in the pathogenesis of vascular cell injury during acute KD, due to their proinflammatory and prothombotic effect on endothelial cells. See Mantovani et al., Immunol. Today 10: 370–74 (1989). Vascular endothelia, in KD lesions, have been demonstrated to express cytokine inducible leukocyte adhesion molecules known to be involved in localization of inflammatory cells. See Leung, supra. Patients with acute KD have been found to have cytotoxic antibodies against IL-1$\beta$, TNF-$\alpha$ and IFN-$\gamma$ stimulated endothelial cells, but not unstimulated cells. See Leung et al., J. Clin. Invest. 77: 1428–35 (1986); Leung et al., J. Exp. Med. 164: 1958–72 (1986).

As indicated, the cause of acute KD and the large scale immune response are unknown. While epidemiologic studies directed toward identifying potential environmental toxins, and laboratory culturing of body fluids for known microbial agents have taken place, an etiological agent has not been found. See Rauch et al., Ped. Infect. Dis. J. 6: 1016–21 (1987). Due to the acute, self-limited nature of the disease, geographic clustering of outbreaks, clinical symptoms of fever and eruptions which mimic conditions and diseases such as measles, roseola, and scarlet fever, as well as the unique susceptibility of young children, it has been suggested that humoral immunity develops early in life. KD is rarely seen over the age of 8, suggesting that there is an asymptomatic infection caused by a ubiquitous agent, followed by development of protective immunity in the general population.

The general observations on KD, as well as other vasculitic conditions, suggest that these diseases may have some similarities with disorders characterized by response to a so-called "superantigen". The patent applications cited supra and incorporated by reference herein, show that various superantigens lead to expanded populations of $V\beta$ elements or TCRs ("T cell receptor molecules"). This evidence is also presented in, e.g., Choi et al., J. Exp. Med. 172: 981–84 (1990); Kappler et al., Science 24: 811–13 (1989); and Choi et al, Proc. Natl. Acad. Sci. 86: 8941–45 (1989). The disclosures of these three references are all incorporated by reference herein. The superantigens, including bacterial toxins, provoke marked activation of T cells and monocytes/macrophages. For example, staphylococcal enterotoxins and streptococcal erythrogenic toxins induce IL-1 and TNF-$\alpha$ from monocytes. Staphyloccal enterotoxin and SPE-mediated stimulation of monocytes is a consequence of binding and transducing a positive signal through MHC-II molecules on monocyte cell surfaces. In the presence of antigen presenting cells, superantigens stimulate T-cell proliferation by selective stimulation of T cells expressing particular $V\beta$ elements. For example, Staphyloccocal TSST-1 stimulates T cells presenting $V\beta 2$. Choi et al., J. Exp. Med. 172: 981–4 (1990), have shown expansion of $V\beta 2$ cells in toxic shock syndrome. The similarities thus suggest at this time that vasculitic diseases especially KD, may involve the same phenomena as is involved in superantigen caused diseases and conditions, but, as noted supra, this is a theory rather than a known mechanism, as compared to the expansion of the Vβ subtype, which is an empirical phenomenon. As noted supra, the inventors do not imply that vasculitic disorders are caused by superantigens.

toid arthritis, one with pauci articular JRA, one child with fever and pneumococcal brain abscess, one adult with scarlet fever, and one adult with fever, rash, lymphadenopathy and jaundice. Table I, reproduced infra, provides demographics.

TABLE 1

| | Demographic Data of Patients and Controls | | | | |
|---|---|---|---|---|---|
| | Acute KD | Conv KD | Healthy Children | Healthy Adults | Disease Controls |
| Number | 14 | 11 | 8 | 12 | 10 |
| Median age | 27 mo | 25 mo | 16 mo | 33 yrs | 5 yrs |
| (range) | (5 mo–11 yrs) | (7 mo–6 yrs) | (7 mo–3 yrs) | (26 mo–40 yrs) | (12 mo–18 yrs) |
| Sex (male:female) | 6:8 | 6:5 | 4:4 | 10:2 | 5:5 |
| Median days after | 6 d | 63 d | | | 5 d |
| onset of fever (range) | (3 d–10 d) | (44 d–153 d) | | | (1 d–10 d) |
| Race or Ethnic group | | | | | |
| Japanese | 10 | 7 | 0 | 6 | 1 |
| Mixed | 2 | 1 | 0 | 0 | 0 |
| Non-Japanese | 2 | 3 | 8 | 6 | 9 |

DETAILED DESCRIPTION OF PREFERRED EMBODIMENTS

EXAMPLE 1

The diagnostic method described herein was developed using nineteen patients exhibiting Kawasaki Disease ("KD" hereafter). The patients, all children, had been admitted to three different hospitals. For the experiments which follow, "acute KD" was defined by criteria including (I) fever; (2) non exudative conjunctival infection; (3) oral pharynx changes including mucosal erythema, dry and fissured lips, "strawberry tongue"; (4) changes in extremities including erythema of palms and soles, edema of hands and feet, or, in the subacute phase of the disease, periungual desquamation; (5) rash and (6) cervical adenopathy (at least one node, 1.5 cm or more in diameter). Fever, plus four of the remaining five indications were required for a diagnosis of acute KD. In addition, the patients could not show clinical and/or laboratory evidence of other diseases known to mimic KD. Blood was drawn before treatment (IVGG) in 14 patients with acute KD (within 10 days of onset of fever), and after 40 days of onset of fever in 11 patients ("convalescent" KD). These data resulted in six paired samples from acute and convalescent stages.

As controls, eight children and twelve adults served as healthy controls, and 10 subjects were studied as disease controls. Of the disease controls, four were children with viral syndromes associated with fever and rash, but who did not fulfill the KD diagnostic criteria discussed supra; one child with culture proven measles; one child with symptomatic systemic juvenile rheuma-

EXAMPLE 2

For patients, blood was drawn as indicated supra, and peripheral blood mononuclear cells ("PBMC") were isolated from heparinized blood using Ficoll-Hypaque density gradient centrifugation, which is a well known and standard technique. These PBMC samples contain T-cells, and to increase production of mRNA for the T cell receptor molecules ("TCRs" hereafter), the T cells were stimulated for three days at 37° C., in an atmosphere with 95% humidity and 5% $CO_2$, using anti-CD3 antibodies (20 ng/ml). The cells were washed, and then expanded for one day in an interleukin-2 containing medium, as described by Choi et al., J. Exp. Med. 172: 981–4 (1990); Kappler et al., Science 244: 811–3 (1989). This methodology has been found to not selectively expand Vβs studied herein, as compared to freshly isolated PBMC.

EXAMPLE 3

Polymerase chain reaction methodology ("PCR") was used to estimate the proportion of T cells expressing a particular Vβ gene segment. The basic methodology is described by Choi et al., Proc. Natl. Acad. Sci. U.S.A. 86: 8941–4 (1989), the disclosure of which is incorporated by reference. In these PCR experiments, total RNA was prepared from stimulated cells, using the acid guanidium-phenol chloroform ("AGPC") method of Chomczynski et al., Anal. Biochem. 162: 156–9 (1987). Two micrograms of total RNA were used for synthesis of the first strand of cDNA. In carrying out the PCR, oligonucleotide primers included a Vβ specific oligomer for one of each of the 22 Vβ families analyzed, as well as an oligomer from downstream Cβ ("constant β") region, as one pair. The second pair of primers included two oligomers from the Cα ("constant α") regions. The primers have been described in Choi et al., supra, and reference is made thereto for specific sequences. It must be noted that certain primers do not distinguish between family members—i.e., the primers for Vβ5.2, Vβ6.1 and Vβ8.1 do not distinguish among Vβ5.2 and 5.3, Vβ6.1, 6.2 and 6.3, and Vβ8.1 and 8.2, respectively. Amounts of cDNA used for each reaction was determined individually, using from one fortieth to one two hundredth of total cDNA. When PCR was used, 23 cycles of amplification were used for Vβ2, 3, 6.1, 7, 8.1 and 13.1, while 25 cycles were used for all others. The difference results from differences in the original mRNA preparations, and was done to ensure that synthesis was proportional.

In order to quantify amplified products, $^{32}P$ end-labeled 3' primers ($\sim 1 \times 10^6$ cpm each) were added to reactions. Amplified products were separated on 2% agarose gels, dried, and analyzed with an Ambis Radioanalytic Image System (AMBIS Systems, San Diego).

Also, input $V\beta$ RNA was analyzed as compared to amplified PCR product obtained. The values showed direct correlation between ratios of PCR product and amount of mRNA.

Figure 1:
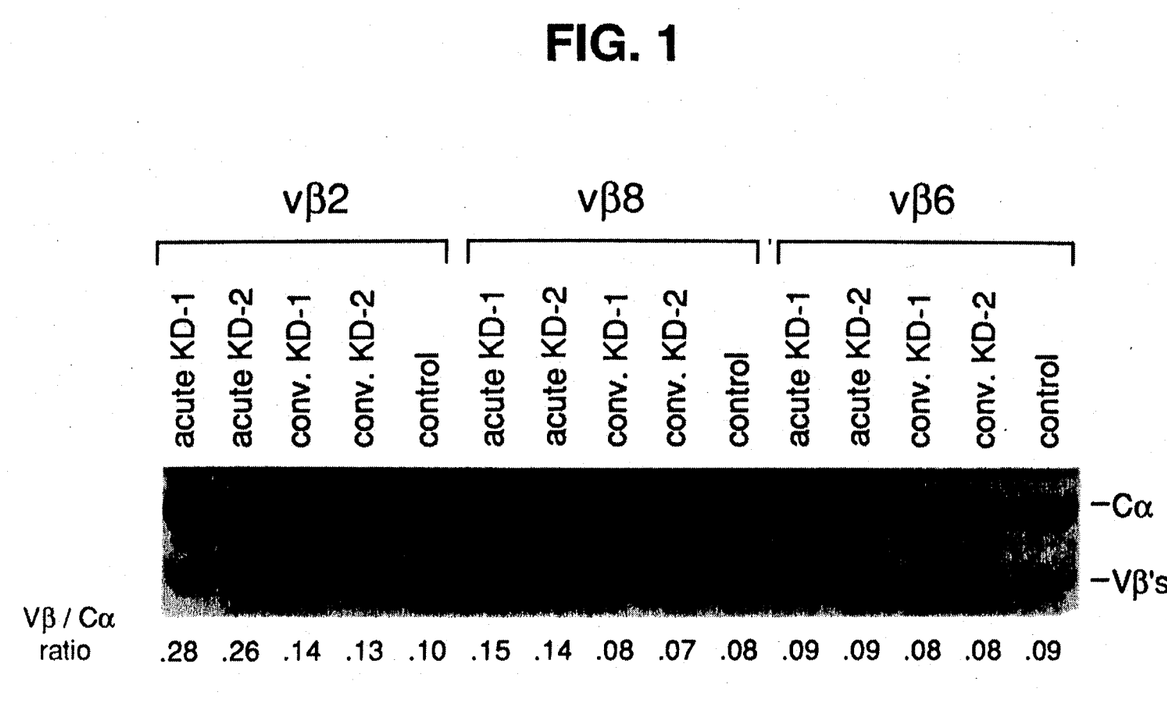
FIG. 1 shows autoradiograms of TCR transcripts as amplified by PCR. Acute, convalescent, and control examples are used.

Results are shown in FIG. 1, using two acute KD patients, two convalescent KD patients, and a healthy child. The binding shows a marked increase in amplified $VB\beta2$ and $V\beta8.1$ cDNA in acute patients as compared to convalescent patients and the control. The $V\beta6.1$ data show little difference.

Figure 2:
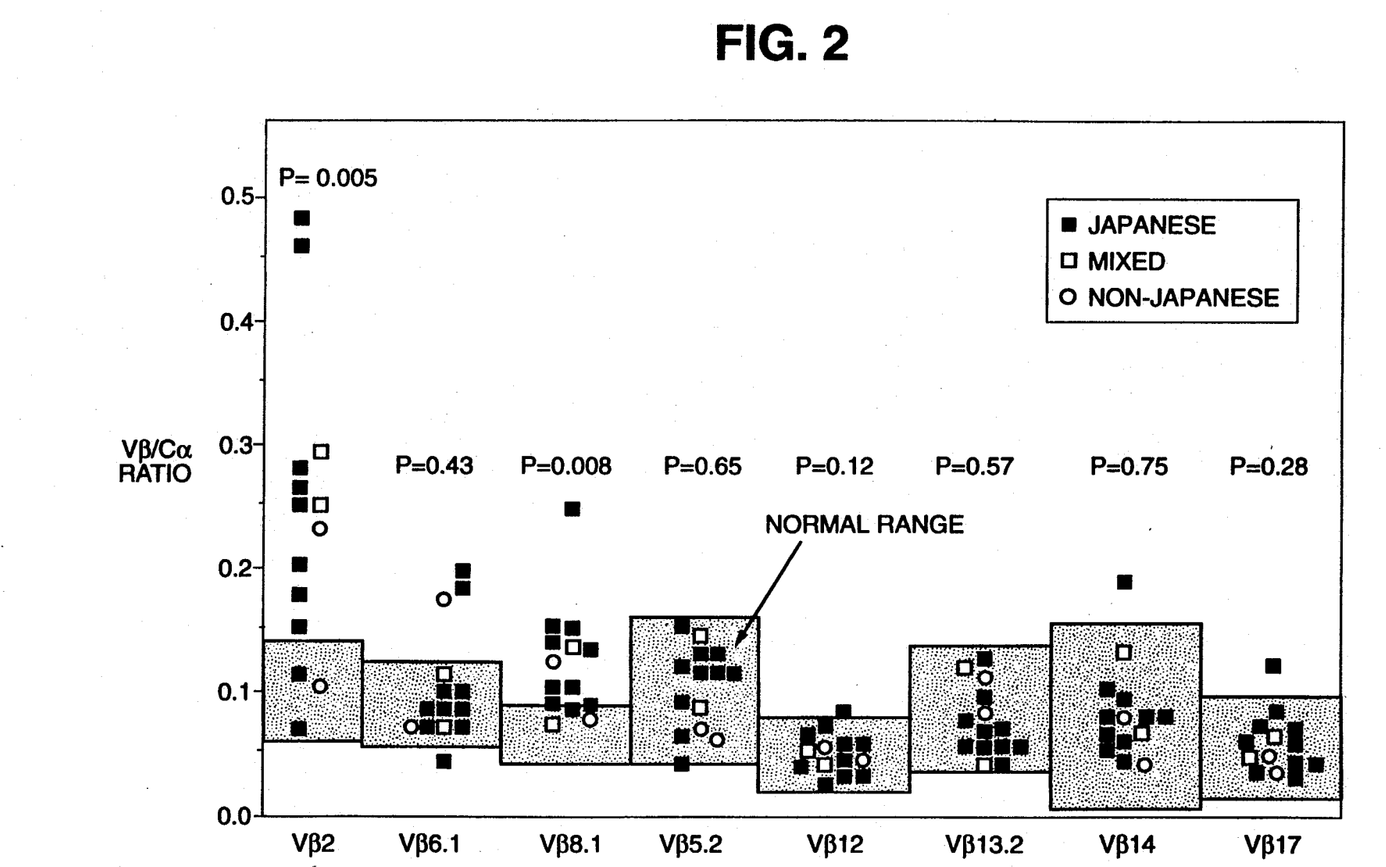
FIG. 2 displays expression of TCR Vβ in the T cells of patients with acute KD.

When total TCR $V\beta$ expression was studied, only $V\beta2$ and $V\beta8$. showed significant increased expression above controls ($V\beta2$:P=0.005; $V\beta8.1$: P=0.008). FIG. 2 shows representative panel of analyses.

Figure 3A:
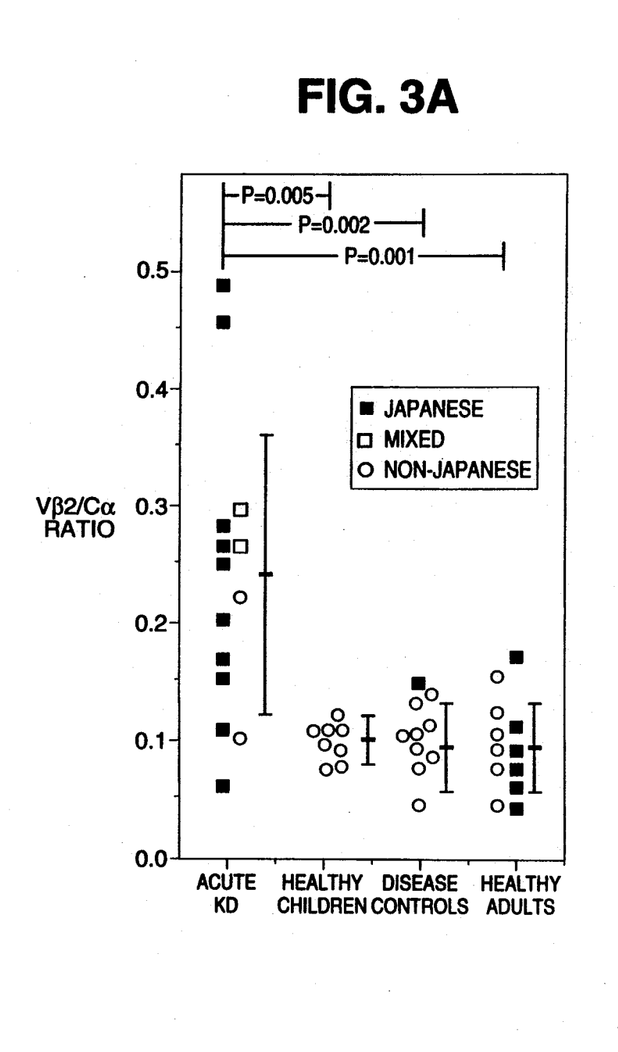
FIGS. 3A and B present data on expression of TCR Vβ2 and Vβ8.1 in T cells from KD patients and control group.
Figure 3B:
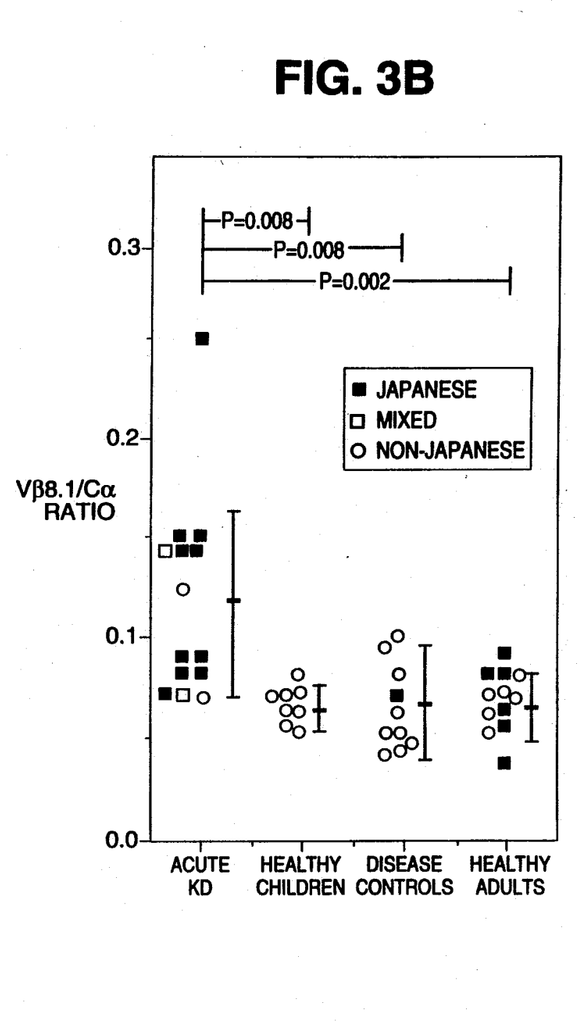
Figure 4:
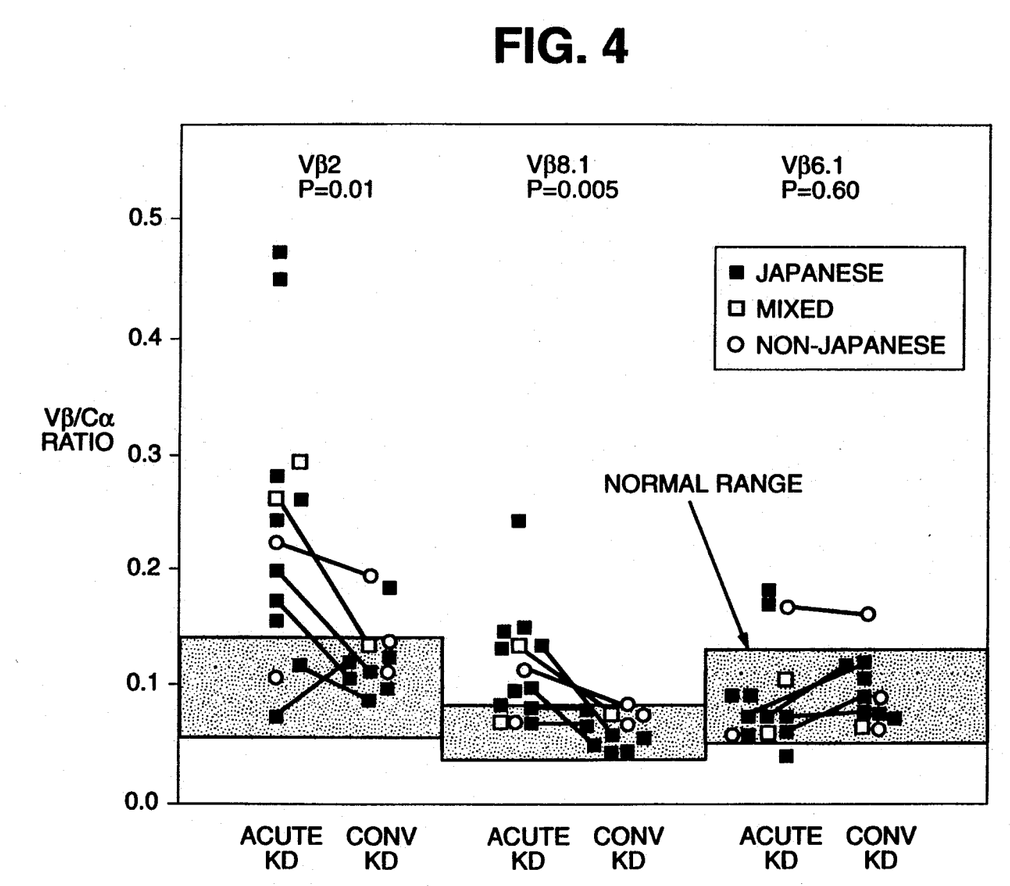
FIG. 4 shows decreases of Vβ2 and Bβ8.1 levels in convalescent KD patients, but not Vβ6.1.

In FIG. 3, mean $V\beta2/C\alpha$ ration is plotted, and it shows a significantly higher value for acute KD patients as compared to controls (mean±SD of 0.24±12, acute KD; 0.10±0.02, healthy children, p=0.005 using paired t test). For out of 14 children with acute KD, the $V\beta2/C\alpha$ ratios were increased by more than 2 standard deviations ("SD") above those for healthy children. A similar pattern is found for $V\beta8.1/Co$ ratios (acute KD: 0.12±0.05; healthy patients; 0.06±0.01, p=0.008). Nine out of 14 acute KD patients had values more than 2 SD above values for healthy children.

Referring to FIG. 3, it should be borne in mind that the highest prevalence of KD is seen in Japan, and 13 out of 19 subjects with KD (68%) were Japanese. To that end, 6 Japanese and 6 non-Japanese healthy adults were tested to determine if ethnic differences affect TCR. FIG. 3 shows that there is no difference, for $V\beta2$ and $V\beta8.1$. It was also determined that there were no differences in any of the $V\beta$ elements, but these results are not shown.

Additional determinations were carried out to see if selective expansion is restricted to acute KD. To do this, T cells from 11 convalescent patients were tested. Only two showed elevated $V\beta2/C\alpha$ ratios more than 2SD above normal. A significant decrease was noted, compared to acute patients. In the case of $V\beta8.1$, no convalescent patients showed elevated ratios. When other $V\beta/C\alpha$ ratios wee studied, it was found that only $V\beta2/C\alpha$ and $V\beta8.1/C\alpha$ ratios showed significant decrease between acute and convalescent phases. These data were generated from the six patients who provided paired samples. Four of these patients showed elevated $V\beta2$ and $V\beta8.1$ during acute KD, and significant drops ($V\beta2$:P=0.04; $V\beta8.1$:P=0.02) between acute and convalescent stages of the illness.

EXAMPLE 4

A second set of assays were carried out using monoclonal antibodies specific for particular $V\beta$ elements. It is important to note that monoclonal antibodies are not available for all $V\beta$ elements known; however, the following experiments used what was available.

Five biotinylated monoclonal antibodies, directed against $V\beta5.1$; $V\beta5.2$, 5.3; $V\beta6.7$, $V\beta8.1$, 8.2; and $V\beta12$ were mixed with samples prepared as described supra, and this mixing was followed by incubation with streptavidin −PE (1/100), and FITC labeled anti Leu 4 (anti CD3) monoclonal antibodies. The resulting complexes may be presented as:

Streptavidin-biotin-mAb-$V\beta$-cell-mAb-FITC.

This material was analyzed using standard fluorescent cell sorting analysis. Forward angle and 90 degree light scatter patterns were used to gate blast cells, which can be easily distinguished from small lymphocytes. Fluorescent intensity was analyzed using a cytofluorograph, and the percentage of T cell blasts bearing each TCR $V\beta$ element was expressed as a percentage of total T cells. (T cells are CD3+).

Figure 5:
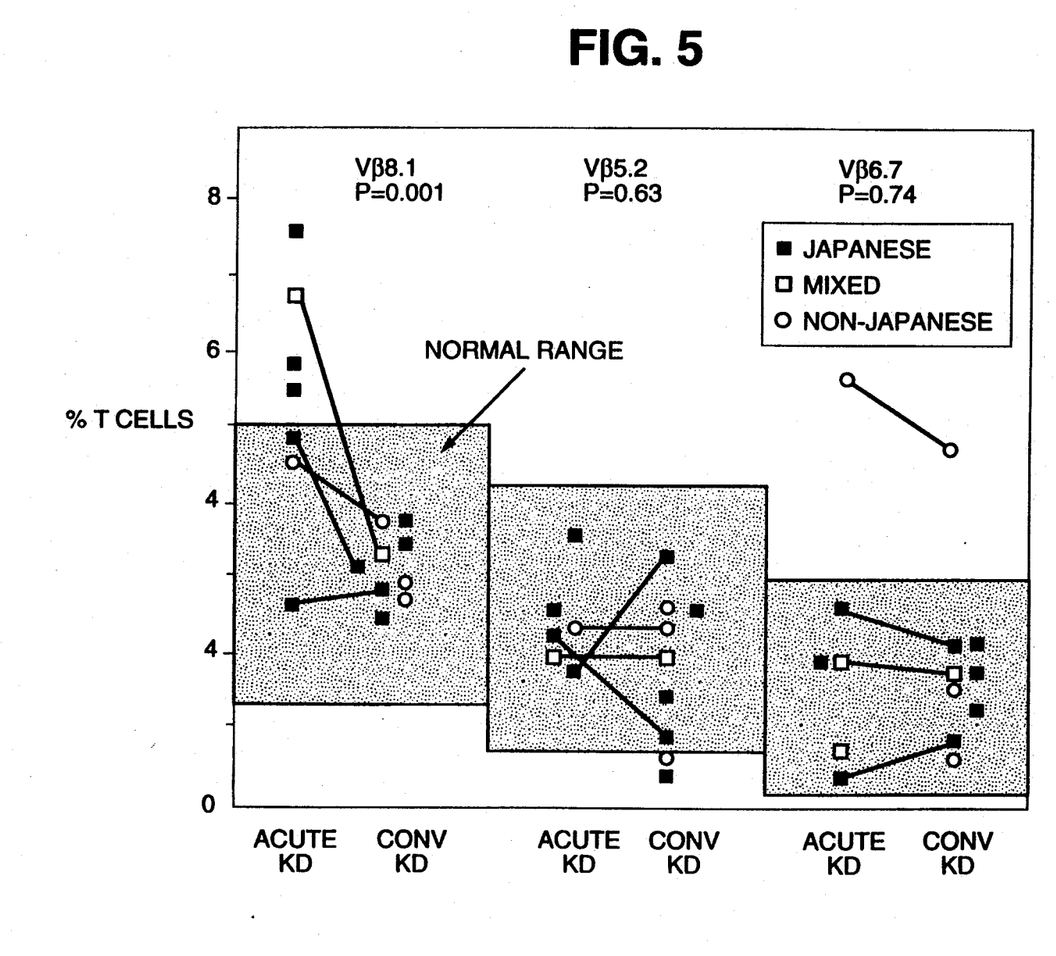
FIG. 5 presents data involving immunological analysis of Vβ elements of acute KD and convalescent KD patients.

The results, presented in part in FIG. 5, showed little difference in the percentage of T cells bearing $V\beta5.1$, 5.2, 6.7 and 12 over acute KD, convalescent KD, and control subjects. On the other hand 4 of out 7 acute KD patients showed increased $V\beta8.1$ levels. When $V\beta8.1$ levels were followed serially in three acute KD patients as they entered convalescence, these dropped to normal levels. Indeed, of the 9 convalescent patients measured none showed elevated $V\beta8.1$ levels.

The foregoing data show that one can diagnose a vasculitic disorder by assaying a T-cell containing sample of a patient believed to be suffering from such a disorder for levels of a particular $V\beta$ element, where abnormal levels of the $V\beta$ element as compared to values in healthy patients are associated with the disorder. Comparison of the levels thus obtained with normal levels permits the investigator to make a diagnosis.

"Vasculitic disorder", as this term is used herein, refers to conditions characterized by chronic or recurrent nodular lesions of subcutaneous tissue. Frequently, such disorders are characterized by obliterative inflammation of arteries and veins. Examples of conditions which are encompassed in this category are given supra.

In determining whether or not to assay for a vasculitic disorder, the diagnostician may consider other parameters, such as those given supra which are characteristic of a particular disorder. All pathological conditions are characterized by various clinical manifestations, which are widely available and need not be repeated here.

The investigator assays a T cell containing sample from the individual being tested. Various materials taken from the body contain T-cells, including blood, synovial fluid, tissue homogenates, and so forth. In addition, the samples which contain T-cells may also contain soluble or free TCRs, and the invention encompasses assaying samples containing these as well.

The method of determination is up to the artisan, various techniques for assaying protein or DNA being known. When PCR is used, one needs primers specific for the RNA of the $V\beta$ element of interest. The amino acid sequences for the $V\beta$ elements are well known, as per Toyonaga et al., Ann. Rev. Immunol. 5: 585-620 (1987), the disclosure of which is incorporated by reference. The development of primers is thus within the ability of the artisan.

Monoclonal antibodies to various $V\beta$ elements are available, and the number is increasing. Exemplary of teachings of specific monoclonal antibodies are Kappler et al., Cell 49: 263-271 (1987); Mak, U.S. Pat. No. 4,923,799; Choi et al., Proc. Natl. Acad. Sci. 88: 8357-8361 (1991); Acha-Orbea et al., Cell 54: 163-273 (1988). When using monoclonal antibodies, the various types of assay well known to the artisan, including ELISA, sandwich, IFA, competitive, RIA, agglutination, and so forth may be used.

Other methods for determining Vβ element levels, including the use of DNA probes, either radiolabelled or labelled with non radioactive materials as per Ward et al., U.S. Pat. No. 4,711,955 may be employed as well.

The observation that certain Vβ subtypes are associated with particular vasculitic disorders suggests a therapeutic approach. One may treat a patient with a particular vasculitic disorder by administering an effective amount of a substance leading to specific deletion of the T-cell subpopulation presenting these Vβ elements. For example, monoclonal antibodies specific for a Vβ2 or Vβ8.1 element may be used, alone or in combination to treat Kawasaki Disease. Of course, the monoclonal antibodies, or other therapeutic agent, such as polyclonal antiserum or antisense DNA which hybridizes to and blocks expression of the Vβ gene, must be nontoxic and pharmaceutically effective (e.g., must have a high enough therapeutic index), but the particulars of choosing these, as well as establishing appropriate dosages, are well known to the skilled artisan.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. Method for screening for possibility of Kawasaki Disease in a patient comprising assaying a T cell receptor containing sample taken from said patient to determine level of Vβ2 or Vβ8.1 by immunoassay or by measuring mRNA expressing Vβ2 or Vβ8.1 wherein the level of Vβ2 or Vβ8.1 or said mRNA is increased in a patient with Kawasaki Disease relative to a normal level; and comparing the determined level to a normal level, wherein an increase in determined level relative to normal level is indicative of the possibility of Kawasaki Disease in said patient.

2. Method of claim 1, wherein said assaying step comprises polymerase chain reaction.

3. Method of claim 1, comprising assaying said sample via an immunoassay.

4. Method of claim 1, wherein said sample contains T cells.

5. Method of claim 1, wherein said sample is a blood sample.

6. Method of claim 1, wherein said Vβ element is Vβ2.

7. Method of claim 1, wherein said patient exhibits a syndrome characteristic of Kawasaki Disease.

* * * * *